(12) United States Patent
Walker et al.

(10) Patent No.: US 6,451,045 B1
(45) Date of Patent: Sep. 17, 2002

(54) HEAT EXCHANGE CATHETER HAVING A HELICALLY WRAPPED HEAT EXCHANGER

(75) Inventors: Blair Walker, Mission Viejo; Nora Pham, Lake Forest; Xochitl Huezo, Rancho Santa Margarita, all of CA (US)

(73) Assignee: Alsius Corporation, Irvine, CA (US)

( * ) Notice: Subject to any disclaimer, the term of this patent is extended or adjusted under 35 U.S.C. 154(b) by 39 days.

(21) Appl. No.: 09/791,391

(22) Filed: Feb. 22, 2001

(51) Int. Cl.$^7$ .................................................. A61F 7/12
(52) U.S. Cl. ........................ 607/105; 607/96; 607/104
(58) Field of Search ................................ 607/105, 113; 604/113

(56) References Cited

U.S. PATENT DOCUMENTS

| | | |
|---|---|---|
| 4,540,402 A | 9/1985 | Aigner |
| 4,546,759 A | 10/1985 | Solar |
| 5,015,230 A | 5/1991 | Martin et al. |
| 5,207,640 A | 5/1993 | Hattler |
| 5,211,631 A | 5/1993 | Sheaff |
| 5,271,743 A | 12/1993 | Hattler |
| 5,279,598 A | 1/1994 | Sheaff |
| 5,304,214 A | 4/1994 | DeFord et al. |
| 5,342,301 A | 8/1994 | Saab |
| 5,383,856 A * | 1/1995 | Bersin ................... 604/101.01 |
| 5,464,437 A | 11/1995 | Reid et al. |
| 5,478,309 A | 12/1995 | Sweezer et al. |
| 5,549,559 A | 8/1996 | Eshel |
| 5,735,816 A | 4/1998 | Lieber et al. |
| 5,749,852 A | 5/1998 | Schwab et al. |
| 5,797,948 A | 8/1998 | Dunham |
| 5,800,375 A | 9/1998 | Sweezer et al. |
| 5,879,316 A | 3/1999 | Safar et al. |
| 5,891,386 A | 4/1999 | Deitermann et al. |
| 5,906,588 A | 5/1999 | Safar et al. |
| 5,957,963 A | 9/1999 | Dobak et al. |
| 6,033,383 A * | 3/2000 | Ginsburg ................... 604/113 |
| 6,056,837 A | 5/2000 | Lieber et al. |
| 6,126,684 A * | 10/2000 | Gobin et al. ................. 604/113 |
| 6,190,356 B1 * | 2/2001 | Bersin ................... 604/101.01 |
| 6,231,594 B1 * | 5/2001 | Dae ........................... 607/106 |
| 6,261,312 B1 * | 7/2001 | Dobak et al. .................. 606/21 |
| 6,264,679 B1 * | 7/2001 | Keller et al. .................... 606/21 |
| 6,287,326 B1 | 9/2001 | Pecor |

FOREIGN PATENT DOCUMENTS

EP  0 853 951 A2  7/1998

OTHER PUBLICATIONS

U.S. patent application Ser. No. 09/133,813, Noda et al., App Pending.
U.S. patent application Ser. No. 09/546,814, Gobin et al., App Pending.
U.S. patent application Ser. No. 09/703,791, Evans et al., App Pending.
U.S. patent application Ser. No. 09/679,399, Noda et al., App Pending.
U.S. patent application Ser. No. 09/704,778, Evans et al., App Pending.
U.S. patent application Ser. No. 09/791,391, Walker et al., App Pending.
Eriksson et al., Intraruminal Fluid Administration to Goats: Effects of Handling and Fluid Temperature, Acta vet. scand., 1994, vol. 35, No. 3, pp. 289–298.

* cited by examiner

Primary Examiner—Linda C. M. Dvorak
Assistant Examiner—H M. Johnson
(74) Attorney, Agent, or Firm—Arlyn Alonzo; Burns Doane Swecker & Mathis

(57) ABSTRACT

A heat exchange catheter has a catheter body with an inflow lumen, an outflow lumen, and an infusion lumen. A first heat exchange balloon helically wraps around at least a portion of the catheter body in fluid communication with the inflow lumen. A second heat exchange balloon helically wraps around at least a portion of the catheter body in fluid communication with the outflow lumen. The first and second balloons form a gap there between to facilitate infusion of fluid into the blood stream of the patient via an infusion port formed within the gap.

27 Claims, 4 Drawing Sheets

US 6,451,045 B1

HEAT EXCHANGE CATHETER HAVING A HELICALLY WRAPPED HEAT EXCHANGER

FIELD OF THE INVENTION

This invention relates to heat exchange catheters, and particularly to catheters that exchange heat with the blood stream of a patient.

BACKGROUND

Heat exchange catheters are used in many instances for a variety of reasons. Some surgeries, for example, are better performed when the patient cools to a hypothermic state. In other instances, a patient may suffer from accidental hypothermia and may need to be warmed to a normothermic temperature e.g. 98.6° F. Some heat exchange catheters include the capability of infusing fluids such as nutrition, medicine and contrast agents into the blood.

Post surgical patients risk infection and fever. A fever can be controlled through the use of a heat exchange system having an intravascular heat exchange catheter. One such system is disclosed in U.S. Pat. No. 6,146,411. This U.S. Patent is incorporated herein by reference and teaches an exemplary system used to achieve patient normothermia.

The principals of heat exchange applicable to any flowing medium (including blood) dictates the amount of heat transfer. In blood, the heat transferred depends on many things including the volumetric flow rate of the blood, the geometry of the heat exchanger and the temperature difference between the heat exchanger and the blood.

Various heat exchange catheter designs have been developed. U.S. Pat. No. 6,126,684, for example, teaches a heat exchange catheter having tubular balloons in serial alignment to exchange heat with the blood stream of a patient. This U.S. Patent is incorporated herein by reference. The balloons allow for a relatively large surface area of contact for heat exchange. Infusion lumen exit ports are defined between the balloons. Unfortunately, these exit port regions limit the effective heat exchange surface area.

Heat exchange catheter balloons can be sized having an external volume that optimally exchanges heat with the flowing blood. The balloon internal volume, however, is large enough to inhibit optimal mixing of the heat exchange fluid. Boundary layers of heat exchange fluid can form in the interior of such balloons, lowering the temperature gradient between the heat exchange fluid at the balloon internal surface and ultimately reducing the effective rate of heat transfer between the heat transfer fluid and the flowing blood.

Heat exchange catheters have been developed that deliver the heat exchange fluid to the distal end of the catheter via an insulated delivery lumen, causing the heat exchange fluid to maintain a relatively uniform temperature until the heat exchange fluid returns via a return lumen to exchange heat with the flowing blood. This improves the temperature gradient between the heat exchange fluid within the interior balloon walls and the flowing blood, unfortunately, the residence time that the heat exchange fluid interacts with the flowing blood is limited.

Blood has a maximum desirable heating limit because above certain temperatures blood proteins can degenerate and coagulation may occur. This limits the maximum operating temperature of known intravasculature catheters. Because the operating temperature of an intravascular catheter is limited, the catheter geometry takes on an increased importance to effectuate overall heat transfer.

What is desired is a heat exchange catheter having a geometry that is optimally designed for transferring heat to flowing blood.

SUMMARY

A heat exchange catheter includes a catheter body having an inflow lumen, an outflow lumen, a proximal region and a distal region. A first balloon helically wraps around at least a portion of the catheter body and maintains fluid communication with the inflow lumen. A second balloon helically wraps around at least a portion of the catheter body and maintains in fluid communication with the outflow lumen. The first and second balloons forming a fluid circuit to facilitate circulation of a heat exchange fluid through the first balloon and the second balloon.

Optimally, the first and second balloons are inflatable from a flattened configuration where the balloons lie flush with the catheter body to an operational configuration where the heat exchange fluid inflates the balloons. The flattened configuration facilitates insertion of the catheter into the body of a patient. Preferably, the catheter inserts into the central vasculature.

The catheter body defines a core extending between the proximal region and the distal region. The inflow lumen and the outflow lumen being defined within the core in the proximal region. The balloons further define the inflow and outflow lumens in the distal region. The core also defines a guidewire lumen.

The first balloon and second balloon wrap around the distal region. According to one aspect of the invention, the balloons define a gap there between. According to an alternate aspect of the invention, the balloons tightly wrap and forms a gap only to expose an exit port. Both of these aspects of the invention include the catheter body defining at least one infusion lumen having an exit port located in the gap.

According to one aspect of the invention, the first balloon and second balloon wrap tightly around the distal region of the core without a gap between the first and second balloon.

According to another aspect of the invention, a sheath surrounds the first and second balloons to inhibit coagulate formation. The sheath is distanced from the first and second balloons according to a variation of the invention. The sheath contacts the first and second balloons according to an alternate variation of the invention.

DETAILED DESCRIPTION

Figure 1:
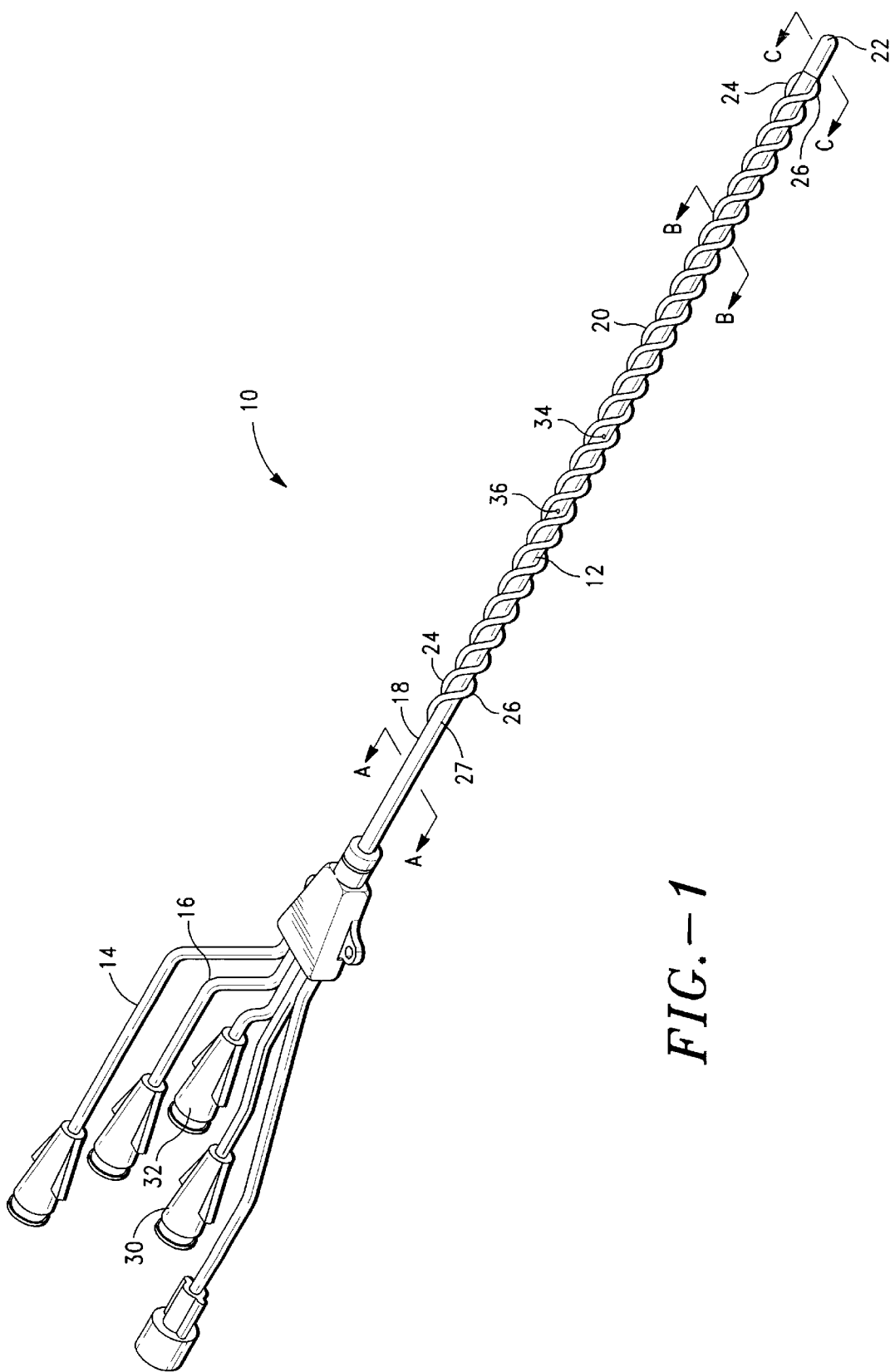
FIG. 1 shows a heat exchange catheter in accordance with the present invention.

FIG. 1 shows a heat exchange catheter, generally designated with the reference numeral 10. The catheter 10 includes a catheter body 12 having an inflow lumen 14, an outflow lumen 16, a proximal region 18, a distal region 20, and a distal tip 22. The catheter 10 also includes a first balloon 24 helically wrapping around the distal region 20 of the catheter body 12 and being in fluid communication with the inflow lumen 14. The catheter 10 further includes a second balloon 26 helically wrapping around the distal region 20 of the catheter body 12 and being in fluid communication with the outflow lumen 16. The first balloon 24 and the second balloon 26 connect in fluid communication in the tip 22 of the catheter body 12 to form a fluid circuit.

The catheter 10 includes an infusion lumen 30 and an infusion lumen 32, which terminate at infusion port 34 and infusion port 36, respectively. The first balloon 24 and the second balloon 26 wrap in a helical pattern to form a helical gap there between. Infusion port 34 and infusion port 36 are located in the helical gap. The infusion lumens 30 and 32 facilitate infusion of fluids such as nutrients, medicines, contrast agents and the like through the infusion ports 34 and 36. According to one aspect of the invention, the catheter 10 defines a centrally located guidewire lumen that also functions to facilitate infusion of fluids.

A heat exchange fluid is pumped via the inflow lumen 14 into the first balloon 24. The heat exchange fluid reaches the tip 22 of the catheter body 12. From the tip 22, the heat exchange fluid returns via the second balloon 26 and the outflow lumen 16.

The temperature, pressure, and flow rate of the heat exchange fluid is regulated externally. It can be appreciated, however, that the catheter 10 can be equipped with sensors and supplemental heating/cooling elements to further monitor and regulate the temperature, pressure and flow rate of the heat exchange fluid. Optimally, the catheter 10 is designed for intravascular use. It is conceivable, however, that the catheter 10 can be used in various internal regions of the body.

The catheter body 12 defines a core 27 extending between the proximal region 18 and the distal region 20. The inflow lumen 14 and the outflow lumen 16 are defined within the core, in the proximal region 18.

Figure 2A:
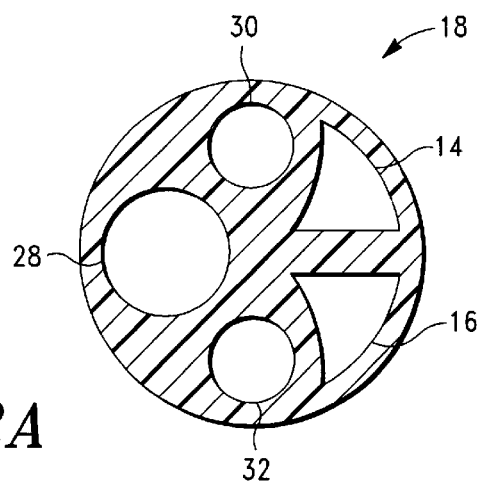
FIG. 2A shows a cross-section of the catheter as seen along line A—A of FIG. 1

FIG. 2A shows a cross-section of the proximal region 18 of the catheter body 12. The proximal region 18 defines a guidewire lumen 28, two infusion lumens 30 and 32. The inflow lumen 14 and the outflow lumen 16 are defined within the catheter body 12.

Figure 2B:
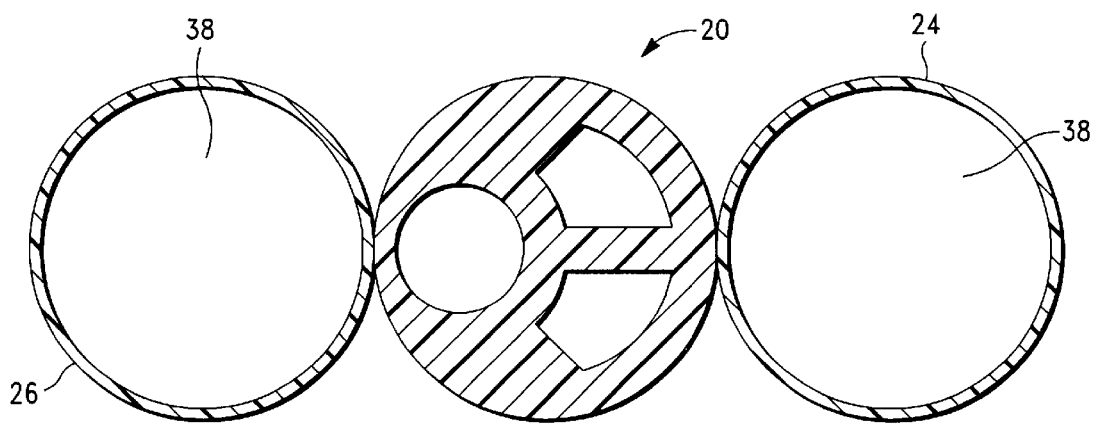
FIG. 2B shows a cross-section of the catheter as seen along line B—B of FIG. 1.

FIG. 2B shows a cross-section of the distal region 20 of the catheter body 12. The balloons 24 and 26 are inflatable from a flattened configuration where the balloons lie flush with the catheter body to an operational configuration. As shown, the balloons 24 and 26 are filled with heat exchange fluid 38, which inflates the balloons 24 and 26 during operation of the heat exchange catheter 10.

Figure 2C:
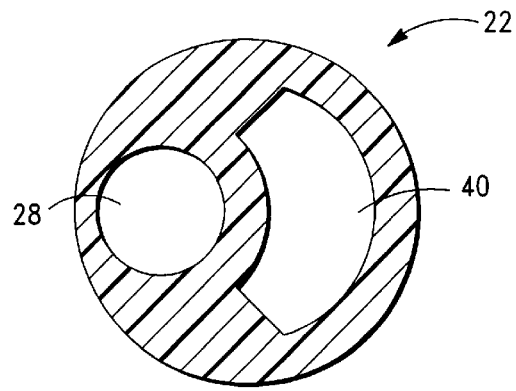
FIG. 2C shows a cross-section of the catheter as seen along line C—C of FIG. 1.

FIG. 2C shows a cross-section of the distal tip 22 of the catheter body 12. The distal tip 22 includes the guidewire lumen 28 and a transition region 40. The transition region 40 joins the inflow lumen and the outflow lumen in fluid communication.

Figure 3:
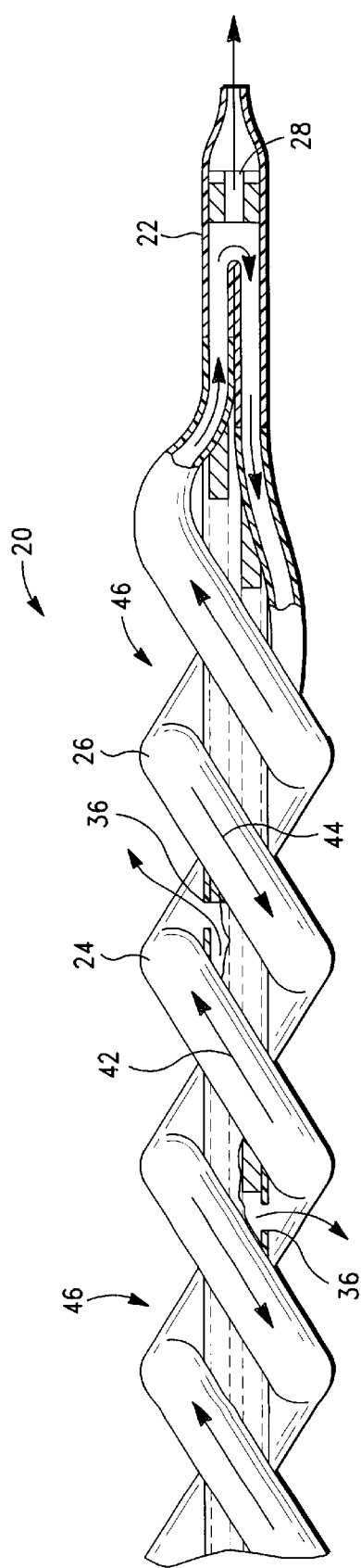
FIG. 3 shows a partial longitudinal-section of the distal region per FIG. 1.

FIG. 3 shows a portion of the distal region 20. The balloon 24 carries the heat exchange fluid in the direction of the arrow 42, towards the distal tip 22. The balloon 26 carries heat exchange fluid in the direction of the arrow 44, away from the distal tip 22. The balloon 24 and the balloon 26 define a gap 46 there between. The gap 46 extends along a helical path between the balloons 24 and 26. The infusion ports 34 and 36 are formed on the distal region 20, within the gap 46.

The gap 46 distances the balloons 24 and 26 to maximize the surface area of the balloons 24 and 26 for heat transfer. Typically blood from a patient's blood stream would flow by the balloons 24 and 26 to heat or cool the patient's body. The gap 46 also enables positioning of the infusion ports 34 and 36 at any desired location along the distal region 20.

According to one aspect of the invention, the guidewire lumen 28 functions to infuse fluids through the distal tip 22.

Figure 4:
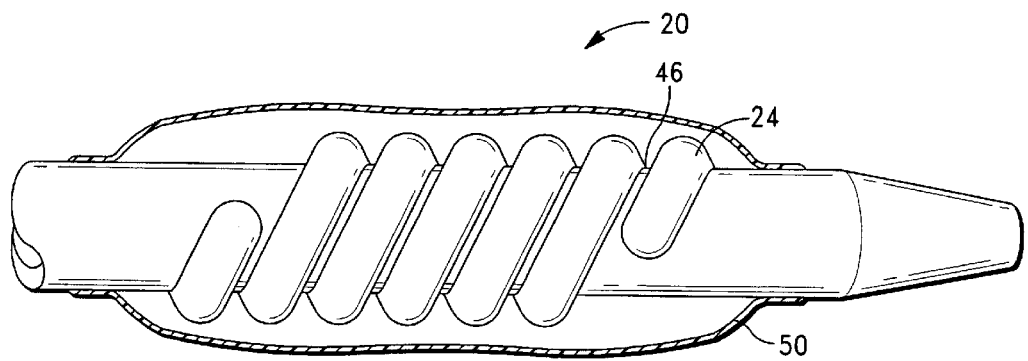
FIG. 4 shows an embodiment of the distal region in accordance with the invention.

FIG. 4 shows a sheath 50 surrounding the balloon 24. The sheath 50 prevents coagulum from forming within the gap 46. The sheath 50 is distanced from the balloon 24 in a radial direction from the distal region 20 according to one aspect of the invention. According to an alternate aspect of the invention, the sheath 50 contacts the balloon 24. According to a further aspect of the invention, an infusion port or ports can be formed within the gap 46.

Figure 5:
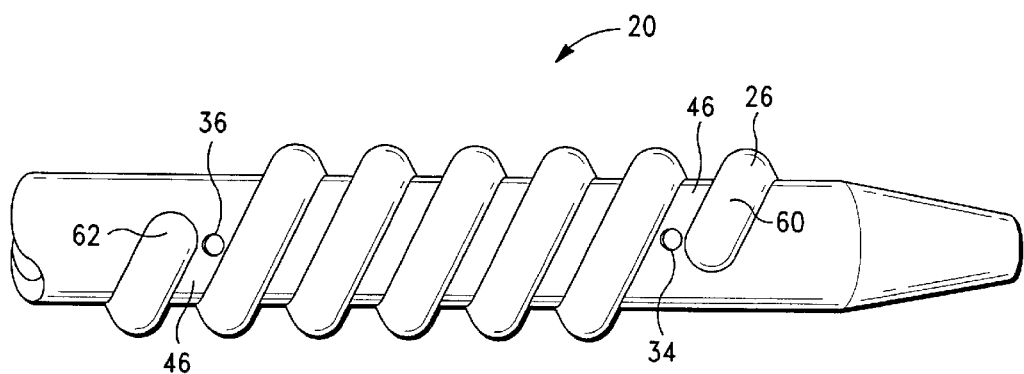
FIG. 5 shows an embodiment of the distal region in accordance with the invention.

FIG. 5 shows a single balloon 26 on the distal region 20. The balloon 26 has ends 60 and 62 and is helically wrapped to form a gap 46 between successive coils. The gap 46 extends along a helical path between the ends 60 and 62. Infusion ports 34 and 36 are positioned near each end 60 and 62 of the balloon 26, and within the gap 46.

Figure 6:
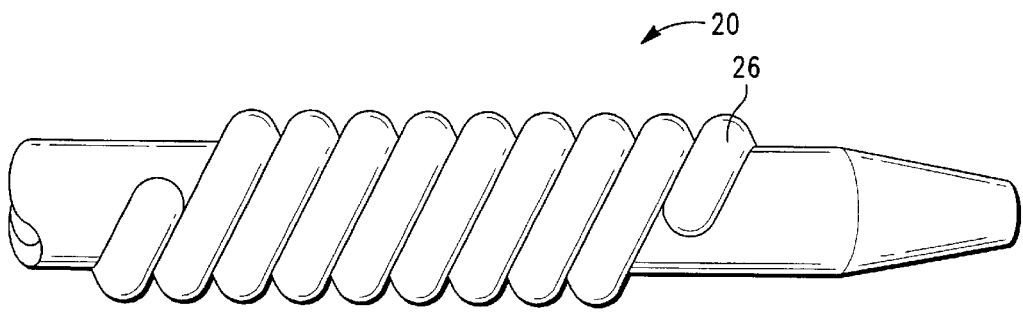
FIG. 6 shows an embodiment of the distal region in accordance with the invention.

FIG. 6 shows a single balloon 36 on the distal region 20. The balloon 36 wraps tightly around the distal region 20, maintaining contact with itself without forming a helical gap. It can be appreciated that when an infusion port formed on the catheter 10 requires exposure, the balloon 36 is conformed with a small gap to expose the infusion port.

IN OPERATION

A method of circulating fluid within a heat exchange catheter includes inserting the heat exchange catheter into the central vasculature of a patient. The proximal portion of the catheter is secured to the patient to prevent catheter movement.

The next step includes circulating a heat exchange fluid through the inflow lumen of a heat exchange catheter. The heat exchange fluid circulates along a helical path to exchange heat with the blood stream of a patient. One benefit of circulating the heat exchange fluid along a helical path is that the residence time that the heat exchange fluid transfers heat is increased compared with tubular heat exchanger systems.

Another benefit circulating the heat exchange fluid along a helical path is that the helical path causes fluid mixing within the catheter. This mixing causes vortices, which disrupts the heat exchange fluid at the boundary layer located at the wall of the inflow and out flow lumens. Further, the helical shape causes blood to flow, turbulently under some conditions, past the heat exchange catheter to improve heat transfer between the heat exchange catheter and the blood.

To add medicine, nutrition, contrast agents and the like, the step of infusing fluid into the blood stream via the heat exchange catheter is performed.

According to one aspect of the invention, the heat exchange occurs through dual helical balloons. One helical balloon circulates fluid from the inflow lumen, the other circulates fluid through the outflow lumen along a helical path. The heat exchange fluid inflates both balloons from a flattened configuration to an operational configuration. Preferably, the operational configuration includes inflating the balloons to a round or an oval cross-sectional configuration.

It can be appreciated that the core of the catheter can inflow heat exchange fluid to the distally mounted heat exchange balloon(s). Alternatively, the balloon(s) can inflow the heat exchange fluid and the core can outflow the heat exchange fluid. Optimally, however, the present invention includes two helical balloons, one inflows heat exchange fluid and the other outflows the heat exchange fluid. Many variations of this concept are possible. Accordingly, the present invention should be limited only by the following claims.

What is claimed is:

1. A heat exchange catheter, comprising:
   a catheter body having an inflow lumen, an outflow lumen, a proximal region and a distal region;
   a first balloon helically wrapping around at least a portion of the catheter body and being in fluid communication with the inflow lumen;
   a second balloon helically wrapping around at least a portion of the catheter body and being in fluid communication with the outflow lumen; and
   the first and second balloons forming a fluid circuit to facilitate circulation of a heat exchange fluid through the first balloon and the second balloon.

2. A heat exchange catheter as set forth in claim 1, wherein the first balloon and second balloon wrap around the distal region, the first balloon and the second balloon define a gap, and the catheter body defines at least one infusion lumen having an exit port located in the gap between the balloons.

3. A heat exchange catheter as set forth in claim 2, wherein the proximal region defines a portion of the inflow lumen and the outflow lumen.

4. A heat exchange catheter as set forth in claim 1, wherein the first and second balloons are inflatable from a flattened configuration where the balloons lie flush with the catheter body to an operational configuration where the heat exchange fluid inflates the balloons.

5. A heat exchange catheter as set forth in claim 1, wherein the catheter body defines a guidewire lumen.

6. A heat exchange catheter as set forth in claim 1, wherein the inflow lumen and the outflow lumen are defined within the proximal region, the first balloon and second balloon wrap tightly around the distal region.

7. A heat exchange catheter as set forth in claim 1, wherein the catheter body includes a transition region that interconnects the inflow lumen and the outflow lumen in fluid communication.

8. A heat exchange catheter as set forth in claim 1, wherein the catheter body includes a distal tip with a transition region that interconnects the inflow lumen and the outflow lumen in fluid communication.

9. A heat exchange catheter, comprising:
   a catheter's body having an inflow lumen, an outflow lumen, a proximal end and a distal end;
   a first balloon helically wrapping around at least a portion of the catheter body and being in fluid communication with the inflow lumen;
   a second balloon helically wrapping around at least a portion of the catheter body and being in fluid communication with the outflow lumen;
   the first and second balloons forming a fluid circuit to facilitate circulation of heat exchange fluid through the first and second balloons; and
   a sheath surrounding the first and second balloons.

10. A heat exchange catheter as set forth in claim 9, wherein the sheath is distanced from the first and second balloons.

11. A heat exchange catheter as set forth in claim 9, wherein the sheath contacts the first and second balloons.

12. A heat exchange catheter as set forth in claim 9, wherein the distal end includes a transition region that connects the inflow lumen and the outflow lumen in fluid communication.

13. A heat exchange catheter as set forth in claim 9, wherein the catheter body defines an infusion lumen.

14. A heat exchange catheter as set forth in claim 13, wherein the first and second balloons define a gap, an infusion port in communication with the infusion lumen is formed within the gap.

15. A method of circulating fluid within a heat exchange catheter, comprising: circulating heat exchange fluid through a heat exchange catheter along a helical path to exchange heat with the blood stream of a patient; and infusing fluid into the blood stream via the heat exchange catheter.

16. A method of circulating fluid within a heat exchange catheter as set forth in claim 15, further comprising circulating the heat exchange fluid through an inflow lumen along a helical path and through an outflow lumen along a helical path.

17. A method, of circulating fluid within a heat exchange catheter as set forth in claim 16, further comprising inflating a first and second heat exchange balloon with the heat exchange fluid.

18. A method of circulating fluid within a heat exchange catheter as set forth in claim 17, wherein the first and second balloons form a gap there between.

19. A method of circulating fluid within a heat exchange catheter as set forth in claim 9, wherein the infusing fluid is accomplished by infusing fluid through an infusion port defined within the gap.

20. A heat exchange catheter, comprising:
   a catheter body having an inflow lumen, an outflow lumen, a proximal region and a distal region;
   a first heat exchange means helically wrapping around at least a portion of the catheter body and being in fluid communication with the inflow lumen;
   a second heat exchange means helically wrapping around at least a portion of the catheter body and being in fluid communication with the outflow lumen; and
   the first heat exchange means and second heat exchange means forming a fluid circuit to facilitate circulation of a heat exchange fluid through the first heat exchange means and the second heat exchange means.

21. A heat exchange catheter as set forth in claim 20, wherein the first heat exchange means and second heat exchange means wrap around the distal region, the first heat exchange means and the second heat exchange means define a gap, and the catheter body defines at least one infusion lumen having an exit port located in the gap between the heat exchange means.

22. A heat exchange catheter as set forth in claim 21, wherein the proximal region defines a portion of the inflow lumen and the outflow lumen.

23. A heat exchange catheter as set forth in claim 20, wherein the first heat exchange means and the second heat exchange means are inflatable from a flattened configuration to an operational configuration.

24. A heat exchange catheter as set forth in claim 21, wherein the catheter body defines a guidewire lumen.

25. A heat exchange catheter as set forth in claim 20, wherein the inflow lumen and the outflow lumen are defined within the proximal region, the first heat exchange means and second heat exchange means wrap tightly around the distal region.

26. A heat exchange catheter as set forth in claim 20, further comprising a sheath surrounding the first heat exchange means and the second heat exchange means.

27. A heat exchange catheter as set forth in claim 26, wherein the sheath is distanced from the first heat exchange means and the second heat exchange means.

* * * * *